United States Patent
Yasovsky (10) Patent No.: US 11,041,853 B2
(45) Date of Patent: Jun. 22, 2021

(54) SENSING SYSTEM AND METHOD FOR DETECTION OF CBM CONTAINING ANALYTES USING THEIR BINDING TO CELLULOSIC SUBSTRATES

(71) Applicant: SENSOGENIC LTD, Rehovot (IL)

(72) Inventor: Alon Yasovsky, Rehovot (IL)

(73) Assignee: SENSOGENIC LTD

( * ) Notice: Subject to any disclaimer, the term of this patent is extended or adjusted under 35 U.S.C. 154(b) by 12 days.

(21) Appl. No.: 16/620,970

(22) PCT Filed: Jun. 14, 2018

(86) PCT No.: PCT/IL2018/050660
§ 371 (c)(1),
(2) Date: Dec. 10, 2019

(87) PCT Pub. No.: WO2018/229775
PCT Pub. Date: Dec. 20, 2018

(65) Prior Publication Data
US 2020/0200744 A1    Jun. 25, 2020

(30) Foreign Application Priority Data
Jun. 14, 2017 (IL) .......................................... 252923

(51) Int. Cl.
*G01N 33/543* (2006.01)
*G01N 33/487* (2006.01)
(Continued)

(52) U.S. Cl.
CPC ....... *G01N 33/54306* (2013.01); *C08B 15/02* (2013.01); *G01N 33/48792* (2013.01); *G01N 33/5308* (2013.01); *G01N 33/5438* (2013.01)

(58) Field of Classification Search
CPC ....... G01N 33/54306; G01N 33/48792; G01N 33/5308; G01N 33/5438; C08B 15/02
See application file for complete search history.

(56) References Cited

U.S. PATENT DOCUMENTS 6,231,733 B1    5/2001  Nilsson et al.
9,201,068 B2    12/2015 Suni et al.
(Continued)

FOREIGN PATENT DOCUMENTS

WO    9733176 A1    9/1997
WO    2006047760 A1    5/2006
(Continued)

OTHER PUBLICATIONS

Ahmad, et al., "Label-Free Capacitance-Based Identification of Viruses", 2015, pp. 1-6.
(Continued)

*Primary Examiner* — Dennis White
(74) *Attorney, Agent, or Firm* — Dorsey & Whitney LLP (57) ABSTRACT

Sensor devices, hand-held probes and systems for use in detection of one or more analyte(s) are presented. The sensor device comprises at least one sensing unit and a measurement unit. The sensing unit comprises a surface by which the sensing unit is exposed to a media when the sensor device is in use, the surface carrying one or more carbohydrate-based compositions immobilized thereon, the carbohydrate-based composition comprises one or more of the following: oxidized cellulose, nano-cellulose, regenerated cellulose, crystalline cellulose and amorphous cellulose, the sensing unit having one or more of its parameters changeable in response to binding between the carbohydrate-based composition and one or more carbohydrate binding modules (CBM) of CBM-containing analyte(s) in the media. The measurement unit being configured and operable to monitor one or more of the parameter(s) of the sensing unit, and upon detecting a change in one of the one or more parameter(s) generating sensing data indicative of the change, thereby enabling detection of the one or more CBM-containing analytes in the media.

20 Claims, 6 Drawing Sheets

(51) Int. Cl.
  *G01N 33/53* (2006.01)
  *C08B 15/02* (2006.01)

(56) References Cited

U.S. PATENT DOCUMENTS

| | | |
|---|---|---|
| 2005/0287552 A1 | 12/2005 | Lin et al. |
| 2012/0264232 A1 | 10/2012 | Kramer et al. |
| 2017/0097342 A1 | 4/2017 | Sundvor et al. |
| 2017/0115267 A1* | 4/2017 | Beauregard .......... C07K 14/001 |
| 2020/0088737 A1* | 3/2020 | Kobayashi ............... C12Q 1/37 |

FOREIGN PATENT DOCUMENTS

| | | |
|---|---|---|
| WO | 2006052891 A1 | 5/2006 |
| WO | 2007084077 A1 | 7/2007 |
| WO | 2009048895 A2 | 4/2009 |
| WO | 2011053234 A1 | 5/2011 |
| WO | 2015017442 A2 | 2/2015 |
| WO | 2016145061 A1 | 9/2016 |

OTHER PUBLICATIONS

Edwards, et al., "Nanocellulose-Based Biosensors: Design, Preparation, and Activity of Peptide-Linked Cotton Cellulose Nanocrystals Having Fluorimetric and Colorimetric Elastase Detection Sensitivity", 2013, pp. 20-28.

Mohamed, et al., "Is Biosensor a Viable Method for Food Allergen Detections?", 2005, 6.

Shani, et al., "Oxidized Cellulose Binding to Allergens with a Carbohydrate-Binding Module Attenuates Allergic Reactions", 2018, 9.

Shoseyov, et al., "Carbohydrate Binding Modules: Biochemical Properties and Novel Applications", vol. 70, No. 2, 2006, pp. 283-295.

International Search Report for PCT/IL2018/050660, dated Nov. 6, 2018.

"Nima." https://www.nimasensor.com/, accessed Mar. 11, 2020.

\* cited by examiner

SENSING SYSTEM AND METHOD FOR DETECTION OF CBM CONTAINING ANALYTES USING THEIR BINDING TO CELLULOSIC SUBSTRATES

TECHNOLOGICAL FIELD

This invention is in the field of sensors, more specifically biosensors, and relates to detection of analytes by their chemical and/or physical characteristics. The invention is particularly useful for identification of allergens in the vicinity of a sensor.

BACKGROUND

Allergies are quite common with increasing rates of sufferers yearly, they badly affect quality of life and some of which are life-threatening. Allergic reactions or diseases include allergic rhinitis (hay fever) (about 20% of the world's population), atopic dermatitis (about 20%), food allergies (about 6%), allergic asthma (up to 18%), and anaphylaxis (up to 2%). Allergies are caused by hypersensitivity and overreaction of the immune system to environmental conditions or various consumed substances, generally called allergens, that typically cause little or no problem in non-allergic people.

Common allergens include pollen, venom, medication and food. Some substances and insect stings may also cause allergies. The underlying mechanism for various allergies involves immunoglobulin E antibodies (IgE), part of the body's immune system, binding to an allergen and then to a receptor on mast cells or basophils where it triggers the release of inflammatory chemicals such as histamine Diagnosis is typically based on a person's medical history, and testing of the skin or blood may be useful in certain cases.

Major food kinds known as containing allergens and causing majority of allergic reactions include milk, soybeans, eggs, wheat, peanuts, tree nuts, fish, and Crustacean shellfish. Sesame, mustard and celery are also recognized as part of the list in some countries.

While it has been found that early exposure to potential allergens and/or the so called allergenimmunotherapy, i.e. gradually exposing people to larger and larger amounts of allergen, can be useful in some allergies types, such as hay fever and reactions to insect bites, it is very effective at food allergies. Avoiding the food that contains allergen(s) can be the most effective and almost the only treatment.

US 2012/0264232 describes a system and method for testing for the presence of antigens for a given food allergy that the user may have. The system comprises two main components, a base station and a test well. The user places a sample of food into the test well. A macerator homogenizes the food in the test well. Antibodies to a particular antigen are bound to an antigen detector in the test well. The base station includes a cartridge dock which powers the macerator and the antigen detector. Antigen-antibody binding provides a change detectable by the detector, which signals the base station of the presence of a threshold degree of antigen-antibody binding and alerts the user of the presence of the antigen, such as by a visual or audible indicator.

U.S. Pat. No. 9,201,068 is directed to a method and apparatus that satisfies the need for a bioelectronic tongue for food allergy detection. The method of detecting concentration of food allergen incorporates antibodies into an electronic tongue to create a bioelectronic tongue. Additionally the method uses impedance, capacitance, and/or other related electrochemical methods for detecting analyte in complex media. The apparatus is a bioelectronic tongue for detecting allergen in diluted food samples, and includes: a sensor array; an impedance or capacitance analyzer; a preprocessor; a feature extractor; a pattern recognizer; and an output device indicating an allergen concentration. In order to implement the method of detecting food allergens on a bioelectronic tongue a computer readable medium containing an executable program is used for performing the analysis of a food sample. The executable program performs the acts of: preprocessing data from an impedance analyzer; extracting a feature pattern; recognizing a pattern of features of data representing a concentration of food allergen contained is the food sample; and outputs allergen concentration data.

U.S. Pat. No. 6,231,733 describes a biosensor in which an immobolized carbohydrate or a derivative thereof is used to generate a detectable signal when a protein, a virus or a cell is bound to the carbohydrate surface. The sensor is an optical sensor, a piezoelectric sensor, an electrochemical electrode or a thermistor. A method of binding carbohydrates to a gold surface is also described.

US 2005/0287552 describes carbohydrate encapsulated nanoparticles. In particular, metallic nanoparticles (e.g. gold nanoparticles) that are encapsulated in biologically important carbohydrate molecules, such as sugars, sugar derivatives, P-blood group antigens and analogues thereof, are described. Methods of employing these carbohydrate encapsulated nanoparticles in diagnostic and therapeutic applications are also described.

The Nima sensor is one of the products on the market which enables detection of gluten in food by utilizing antigen-based chemistry and a finely tuned optical sensor (www.nimasensor.com).

GENERAL DESCRIPTION

The present invention provides for a novel technique for the detection of a variety of chemical and/or biological substances, including analytes, such as allergens, including but not necessarily limited to those found in a variety of food sources, some of which are listed above, and biological organisms, e.g. viruses and/or bacteria, that have specific characteristics. In contrast to the majority of known solutions which are single-analyte or single-allergen detection mechanisms, e.g. capable of detecting presence of one specific allergen, the technique of the present invention allows for detection of all of the analytes (e.g. allergens) in a media (multi-analyte or multi-allergen media) by a single, yet powerful solution.

The present invention allows for portable and mobile sensing device for home-use, thereby enhancing the usability, availability and convenience.

Further, the present invention enables the identification of the certain/specific kind of analyte or allergen. Also, specific identification of each one of a plurality of analytes or allergens present in an examined sample, by running a single examination process, is one of the present invention's capabilities.

According to the technique of the invention, the sensing is based on a molecular binding domain which is common to a large number of the concerned analytes (e.g. viruses, bacteria) and/or allergens that cause the food allergies and respiratory allergies. Generally, the detectable analyte, is (in the case of allergen) or includes (in the case of a bacteria, for example) a specific kind of protein that includes a defined functional binding site, called the carbohydrate-binding module (CBM), that causes binding of the analyte/protein/ allergen to specifically known materials, as will be described further below. The defined functional binding site, the CMB, is common to a plurality of analytes/allergens, therefore by using the right material that binds to the analyte/protein/allergen, the present invention provides a powerful technique for detection of all the CBM-containing analytes/proteins/allergens via a single sensing device. As mentioned, it is noted that the technique of the invention can be usefully practiced to detect biological organisms based on the inclusion of a CBM mechanism in such organisms. Such biological organisms include, for example, viruses, bacteria, toxin and fungal.

In "Oxidized Cellulose Binding to Allergens with a Carbohydrate-Binding Module Attenuates Allergic Reactions", *The Journal of Immunology*, 2011; 186:1240-1247; the researchers have shown that the polysaccharide (carbohydrate) Oxidized Cellulose (OC) demonstrates a strong and relatively specific allergen-binding capacity to CBM-containing allergens. The researchers concluded that OC's ability to attenuate allergic inflammation by binding to allergens and promoting allergen airway clearance, in addition to its documented safety record, forms a firm basis for its application as an alternative treatment for prevention and relief of allergy and asthma.

In some exemplary embodiments, the present invention provides for a sensor for detection of allergens, specifically in food samples, such that the sensor utilizes the affinity of allergens to bind to a carbohydrate through the CBM mechanism included in the allergens. The CBM mechanism is of high specificity and allows for detection of the bound allergens by a novel technique as described herein.

Once the CBM-based chemical binding between the analyte/protein/allergen and the carbohydrate-based composition takes place and is detected according to the technique of the invention, the present invention also enables the specific identification of the bound one or more analytes/proteins/allergens.

According to the invention, the sensor is configured such that at least one characteristic (parameter/property) of the sensor is changeable in response to the binding of the CBM-containing substance (analyte/protein/allergen) to the carbohydrate-based composition immobilized to a surface of the sensor. The at least one changeable parameter/property is specific to the bound analyte/protein/allergen(s), such that it enables the identification of the one or more bound analytes/proteins/allergens.

It should be noted that while the invention is more specifically illustrated with respect to identification of such substance as allergen, it is appreciated by those skilled in the art, that the technique of the invention can be applied, with suitable adjustments, to other substances that contain CBM. Those substances contain one or more proteins that include the CBM(s). Therefore, whenever a specific illustration mentions allergens, it can be similarly applied to other substance containing CBM (e.g. analyte(s) that contain protein(s) containing CBM(s)), and the expressions "protein" and "allergen" should be interpreted broadly such that they encompass an analyte.

It should also be noted that the expressions CBM-containing substance, analyte, protein and allergen can be used herein interchangeably to describe a material containing one or more CBM(s) that can be detected according to the technique of the present invention.

Thus according to a first broad aspect of the present invention, there is provided a sensor device for use in detection of one or more analytes (substances). The sensor device comprises:

at least one sensing unit having a surface by which the sensing unit is exposed to a media when the sensor device is in use, said surface carrying one or more carbohydrate-based compositions immobilized thereon, the sensing unit having one or more of its parameters changeable in response to binding between said carbohydrate-based composition and one or more carbohydrate binding modules of (CBM)-containing analytes (substances) in the media based on the CBM domain, and a measurement unit configured and operable to monitor said one or more parameter(s) of the sensing unit, and upon detecting a change in at least one of said one or more parameter(s) generating sensing data indicative of the change, thereby enabling detection of the one or more CBM-containing analytes (substances) in the media.

It should be understood that depending on the requirements of a specific application, detection of the one or more CBM-containing substances in the media may include identification of the presence of the one or more CBM-containing substances in the media, or may also include specific identification of the one or more CBM-containing substances in the media.

The sensing unit may be configured with at least two of its parameters/properties changeable in response to the binding between the carbohydrate-based composition and the one or more CBM-containing analytes (substances) in the media. The measurement unit may be configured and operable to monitor a first changeable parameter of the at least two changeable parameters, and upon detecting a first change in the first parameter generating a first sensing data indicative of the first change, and enabling monitoring a second changeable parameter of the at least two parameters and generating a second sensing data indicative of the second change. Alternatively, the measurement unit may be configured for concurrently and independently monitoring the first and second parameters/properties to detect changes in these parameters. Moreover, the sensor device may include, as described further below, more than one sensing unit, each having one or more changeable parameters in response to the binding between the carbohydrate-based composition and one or more carbohydrate binding modules of (CBM)-containing substance in the media. In any one of these examples, the sensing data thus comprises the first and second sensing data pieces.

The sensing unit may be configured such that one or more changeable parameters thereof include dielectric property of one or more parts of the sensing unit. The measurement unit may be configured and operable to monitor the dielectric property over a frequency spectrum and generate the sensing data comprising a frequency spectrum response indicative of the one or more CBM-containing analytes in the media.

In some embodiments, the sensing unit may comprise an antenna structure having at least a portion thereof formed with the carbohydrate-based composition coating, and the changeable parameter(s) may comprise permittivity reflection parameter of the antenna structure. Alternatively, or additionally, the sensing unit may comprise a capacitor structure, and the changeable parameter(s) may comprise capacitance of such capacitor.

The changeable parameter(s) of the sensing unit may include weight of one or more parts of the sensing unit.

In some embodiments, the sensing unit may include a quartz crystal microbalance (QCM) resonator, and the changeable parameter(s) may comprise frequency and/or resonance condition of the quartz crystal microbalance (QCM) resonator. For example, the sensing unit may comprise an antenna structure integrated in said quartz crystal microbalance (QCM) resonator. The configuration may be such that the sensing unit includes an electrodes' arrangement, in which one or more electrodes is/are part of the QCM resonator carrying the carbohydrate-based composition, and one or more other electrodes is/are part of the antenna structure, in which case the antenna structure may or may not carry the carbohydrate-based composition.

In some embodiments, the measurement unit comprises a radiation detector configured and operable to monitor radiation reflected from or transmitted through or emitted by one or more parts of the sensing unit. The radiation may have frequencies in Infrared (IR) or Ultraviolet (UV) or visible light ranges.

In some embodiments, the sensing unit comprises carbon nanotube structure. The one or more changeable parameter(s) comprise(s) photoluminescence of one or more parts of the carbon nanotube structure.

In some embodiments, the one or more changeable parameter(s) comprise(s) a color of one or more parts of the sensing unit.

As described above, for some applications of the sensor device of the invention, specific identification of the one or more CBM-containing substances in the media is needed. The sensor device may thus be associated with an analyser unit configured and operable to receive and analyze the sensing data, and generate output data indicative of the specific identification of the one or more CBM-containing analytes in the media. In some embodiments, the sensor device is configured and operable to communicate with the analyser unit being an external analyzer (e.g. at a cloud computer) by conveying (transmitting) the sensing data thereto; or the sensor device may comprise such analyzer unit as an internal part thereof; or the analysing software is properly distributed between an internal analyzer in the sensing device and an external analyzer, e.g. at a cloud computer. In case the use of external analyzer is considered (at least for partial processing and analysing of the sensing data), the sensor device is installed with a suitable communication unit configured and operable for data communication with the external analyzer unit, via a communication network, to convey to the external analyzer unit said sensing data and associated identification data assigned to the sensor device (any known suitable data exchange technique and communication protocols, e.g. that of cloud computing). The analyzer unit (in either one of internal, external or combined/distributed configurations) may be configured and operable to access database comprising data about a plurality of CBM-containing analytes, i.e. comprising, for each analyte, a number of associated signatures corresponding to changes of the one or more changeable parameters of the corresponding sensing units or sensing unit types each having associated identification data, to thereby determine whether the media contains specific one or more CBM-containing analytes.

The sensor device may be configured and operable, when in use, to expose the sensing unit (e.g. its surface carrying the one or more carbohydrate-based compositions immobilized thereon) to the media comprising one or more of the following foods: milk, eggs, soy, nuts, peanuts, sesame, wheat, celery, fish, and shellfish.

The CBM-containing analyte(s) may comprise one or more protein(s), allergen(s), virus(es), bacteria.

The carbohydrate-based composition may comprise one or more of the following: oxidized cellulose, nano-cellulose, regenerated cellulose, crystalline cellulose and amorphous cellulose.

In some embodiments, the sensor device comprises a plurality of sensing units comprising sensing units carrying different kinds and/or amounts of carbohydrate-based compositions immobilized thereon to be exposed to the same media, such that the one or more changeable parameters of the different sensing units change in different way(s) in response to said binding. The analyzer unit may thus be configured and operable to receive the sensing data from each of said plurality of sensing units, and upon detecting a corresponding plurality of changes of the one or more changeable parameters of the sensing units, generating a corresponding plurality of output data indicative of specific identification of the one or more CBM-containing analytes in the media.

In some embodiments, at least a part of the sensing device containing the sensing unit(s) is disposable.

The sensor device may comprise one or more feeding mechanisms configured and operable for feeding a sample of the media towards said at least one sensing unit, feeding washing agent media that removes materials that did not bind to the immobilized carbohydrate-based composition, and/or feeding a regeneration agent that removes materials that have bound to the immobilized carbohydrate-based composition, to thereby prepare the sensing unit(s) for another detection cycle. The feeding mechanism may comprise one or more of the following: a heating utility, an ultrasonic utility and a ventilation utility.

The sensing unit may be configured and operable to be exposed to the media being in gas or liquid phase.

The invention in its another aspect provides a sensor device for use in allergen detection in a vicinity thereof, the sensor device comprising:

a sensing unit carrying on at least a portion thereof a carbohydrate-based composition comprising one or more of the following: oxidized cellulose, nano-cellulose, regenerated cellulose, crystalline cellulose and amorphous cellulose, and configured to expose the carbohydrate-based composition on said at least portion of the sensing unit to a media when the sensor device is in use, the sensing unit having one or more of its parameters (characteristics, properties) changeable in response to binding between said carbohydrate-based composition and one or more carbohydrate binding modules of (CBM)-containing proteins in the media based on the CBM domain, and a measurement unit configured and operable to monitor at least one of the one or more changeable parameter(s) of the sensing unit, and upon detecting a change in the at least one changeable parameter generating sensing data indicative of the change, thereby enabling detection (and possibly also specific identification) of the one or more CBM-containing proteins in the media.

The invention, in its yet another aspect provides a handheld probe comprising the above-described sensor device and being configured to be brought in proximity to the media when in use.

In yet further aspect, the invention provides an analyte detection system being part of or connected to a communication network. The analyte detection system comprises:

an input utility configured and operable for independently receiving, via the communication network, one or more input data pieces, the data piece comprising sensing data indicative of interaction of a sensor device with a media and identification data of said sensor device comprising data about one or more carbohydrate-based compositions carried by the sensor device;

a processor utility configured and operable for analyzing the input data pieces, and determining for each of the input data pieces whether the respective sensing data is indicative of the sensor device interaction with a media containing analyte, said analyzing comprising: for the sensing data piece being indicative of a change in one or more of the changeable parameters of the sensor device, determining whether said change corresponds to a condition of the media classifying it as analyte-containing media, said determining comprising accessing database comprising data about a plurality of analytes comprising, for each analyte, associated signature changes of the one or more parameters of the sensor device and the identification data of the sensor device; and an output utility configured and operable for generating output data indicative of the analyte, to be transmitted via the network to a user of the respective sensor device.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
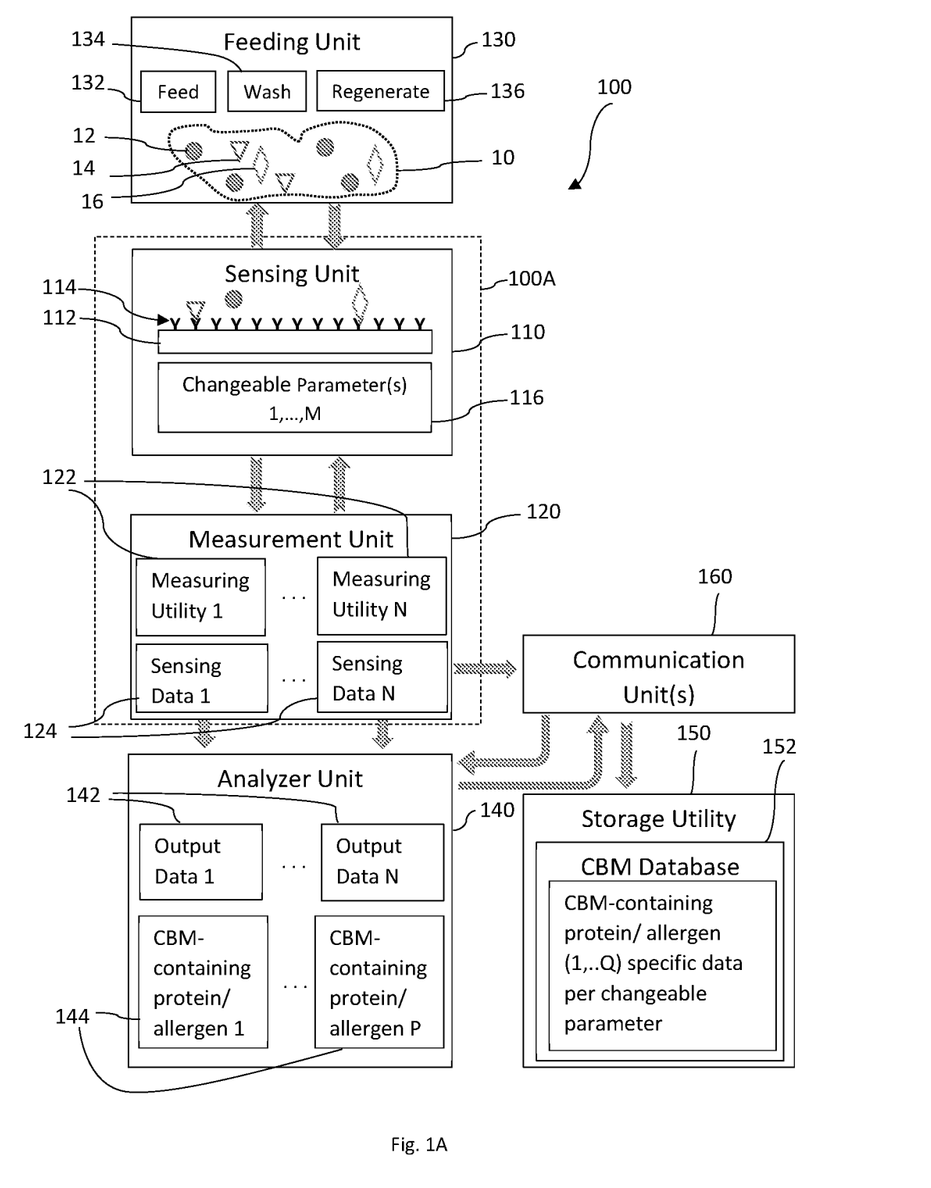
FIG. 1A is a block diagram an example of a sensor device of the present invention.

Reference is made to FIG. 1A illustrating schematically in a block diagram a non-limiting example of a sensor device 100 according to exemplary embodiments of the present invention. The sensor device 100 is configured as a biosensor configured and operable for detection of substances and/or analytes (such as proteins) in a media 10 under examination. In specific non-limiting applications of the present invention, as will be described herein, the media 10 is a kind of food, and the proteins to be detected are allergens. It should be noted, however, that the technique of the invention can be practiced to detect other biological molecules or organisms in a food or non-food media, such as detection of certain kinds of viruses, fungal and others. As shown in the figure, the sensor device 100 includes a sensing unit 110 that is configured and operable to chemically bind the concerned substances/analytes (e.g. proteins) which exist in the media 10 under examination, and a measurement unit 120 configured and operable to measure one or more parameters of the sensing unit 110 that change in response to the binding of the concerned analytes (proteins) to the sensing unit 110. The sensor device 110 can be configured with the sensing unit 110 and the measurement unit 120 only, as illustrated by the dashed box 100A, while the rest of the units/utilities, as will be described below, can be either included in the same enclosure of the sensor device 100 or be external to the sensor device 100 while interacting with sensor device 100 via suitable connection/communication facilities. Accordingly, as further shown in FIG. 1A, the sensor device 100 includes a feeding unit 130, an analyzer unit 140, a storage utility 150, and one or more communication units 160 that can be included in the sensor device 100 to enable communication with external units or utilities. In case the sensor device includes external units and utilities, such as the analyzer unit and storage utility, it will be equally called herein as a sensor system, without limiting the broad meaning of the sensor device.

The sensor device 100 includes one or more sensing units 110 (only one is shown in the figure). The sensing unit 110 includes a sensing surface 112 configured and operable to carry at least one receptor 114 immobilized thereon to be exposed to the media 10 when the sensor device is in use. It is noted that, the sensing surface 112, as mostly used herein, means a functional surface formed by the immobilized receptor and does not necessarily mean a physical surface with given dimensions, although it can be as the case may be and as will be further exemplified below.

The sensor device 100 utilizes the carbohydrate binding module (CBM) found in a plurality of proteins, specifically allergens, that enables the substance(s)/analyte(s) that contain the protein(s) to bind to specific receptors. The receptor 114 of the sensing unit 110 is chosen from a family of receptors that bind to molecules or organisms that contain the CBM. Specifically, carbohydrates are known for their affinity and capability to bind to CMB containing molecules or organisms. Consequently, the receptor 114 is configured, in some embodiments, as a carbohydrate-based composition that binds to a CBM-containing protein (which, by turn, is included in the analyte under examination). More specifically, the receptor 114 can include one or more of the following, known for their high affinity/binding to CBM-containing proteins in general and to CBM-containing allergens in particular: oxidized cellulose, nano-cellulose, regenerated cellulose, crystalline cellulose and amorphous cellulose. Generally, the tested media 10, such as a food, includes media constituents, such as 12, 14 and 16, that can be CBM-containing proteins/molecules/organisms, aka analytes, and non-CBM-containing proteins/molecules/organisms. Only the CBM-containing proteins/molecules/organisms will bind to the chosen receptor(s) 114. In the described example, as shown, the media constituents 14 and 16 contain CBM and therefore are bound by the receptor(s) 114 forming respective CBM-based conjugants, while the constituent 12 does not contain CBM and therefore is not bound by the receptor(s) 114.

In order to detect binding of the CBM- containing proteins or, in general, CBM-containing analytes, such as 14 and 16, to the sensing surface 112 which includes the immobilized receptor(s) 114, the sensing unit 110 has one or more of its parameters (1, . . . M) 116 changeable in response to the CBM-based binding reaction. The measurement unit 120 has one or more measuring utilities (1, . . . N) 122 configured for measuring/monitoring the value (or the change in the value) of the changeable parameters of the sensing unit 110. It should be noted that the number of the measuring utilities 122 is not necessarily the same as the number of the changeable parameters 116. They can be either equal or different. For example, it can be that one measuring utility is capable of measuring two or more changeable parameters or the opposite way around.

As mentioned, the sensor device 100 includes one or more sensing units 110, which can be identical or different. If more than one sensing unit 110 is included, they can have same or different kinds of receptors, concentration or amount of receptors, sensing surfaces, and changeable parameters. This enables the sensor device to provide one or more of the following: control vs. test for any examined media constituent, comparative results for the examined media constituent, binding of different CBM-containing media constituents to differently characterized receptors, highly specific binding capabilities of different media constituents to different receptors, etc. In case more than one sensing unit is included in the sensor device, or in case there are more than one sensor device each with its sensing unit, identification data of each sensing unit or sensor device may be available to identify each sensing unit or sensor device. the identification data may include data about the carbohydrate-based composition(s) carried by the sensing unit or sensor device. In one preferred embodiment, the sensing unit 110 includes one kind of receptor 114 capable of binding to a plurality of CBM-containing media constituents, specifically CBM-containing proteins and more specifically CBM-containing allergens.

The measurement unit 120 can be a separate component or it can be integrated, fully or partially, within the sensing unit 110. In other words, it should be understood that the sensing and measuring units, 110 and 120, are defined as functional components of the sensor device, which can be incorporated within separate structures or in a single integrated structure. For example, the sensing surface 112 can be a passive substrate holding the receptor(s) 114 or it can be an active structure, such as a piezoelectric material, forming a substrate and a measuring utility at the same time. In the latter non-limiting example, the changeable parameter 116 can be a mechanical stress or vibration monitored and measured via electrical signals generated by the piezoelectric material of the sensing surface as a result of a mechanical stress applied thereto by the binding of the CBM-containing proteins. Non-limiting examples of the possible configurations of the sensing unit are described further below.

The measurement unit 120 monitors/measures the changeable parameter(s) via its measuring utilities (1, . . . N) and generates respective number of sensing data (1, . . . N) 124. Then, the measurement unit 120 communicates with the analyzer unit 140 to send the sensing data 124 to the analyzer unit 140 for processing. In case the analyzer unit 140 is not included within the same enclosure with the measurement unit 120, the sensor device 100 includes communication unit(s) 160 configured for connecting between the measurement unit(s) 120 and the analyzer unit 140 to thereby enable exchanging data therebetween. The communication unit(s) 160 can be distributed between the measurement and analyzer units to enable effective communication and transfer of data. The communication unit(s) 160 can be configured to use any communication technique known in the art, be it wired or wireless communication, such as, but not limited to, RF, Bluetooth, IR, server-based communication, internet-based communication or other.

The analyzer unit 140 is generally a software program or a software/hardware combination. When configured as a software, it can be configured to run on a dedicated hardware or on a generic computing device. The analyzer unit 140 is configured and operable for receiving and processing the sensing data 124 to thereby generate respectively corresponding output data (1, . . . N) 142 indicative of the CBM-containing analytes that were bound by the receptor 114, e.g. media constituents 14 and 16 in the described example. Generally, each output data 142 is the outcome of analysis performed on a respective sensing data 124 that originates from a respective measuring utility 122.

The measuring utility 122 is responsive to the sensing data from the sensing unit(s) and measures/monitors one or more changeable parameters 116 of the sensing unit 110. The one or more changeable parameters 116 change in response to the binding of one or more CBM-containing analytes by the receptor 114. As mentioned above, in the preferred situation where one receptor 114 (e.g. oxidized cellulose) is used for binding and detection of more than one CBM-containing analyte (protein, allergen, etc.), and even in case of using one measuring utility 122 to measure/monitor one changeable parameter 116, the sensing data 124 as well as the corresponding output data 142 is indicative of the change in the changeable parameter 116 where the change is in response to the binding/detection of all the CBM-containing analytes (proteins, allergens, etc.) that were bound by the receptor 114. In other words, the output data N corresponding to the sensing data N includes accumulated information about all the CBM-containing analytes that were bound, e.g. media constituents 14 and 16. According to the present invention, it is possible to identify each one of the bound CBM-containing analytes by utilizing the superposition principle. The accumulated information in each output data (1, . . . N), corresponding to the different bound CBM-containing analytes, is disassembled to analyte-specific data, thereby enabling identification of each bound CBM-containing analyte (1, . . . P) 144, as will be further described and exemplified below.

According to the invention, the analyzer unit 140 uses a predefined CBM database 152 included in a storage utility 150 to identify the specific CBM-containing analytes (proteins, allergens, . . . ). In some embodiments, both of the analyzer unit and storage utility are included in the sensor device. In some other embodiments, one or both of them is/are not included in the sensor device, and in this case the analyzer unit and the storage utility can be included in a common enclosure or can be separate. In the latter case, the analyzer unit is configured to access the CBM database in the storage utility via communication techniques known in the art, as was described above with respect to the measurement and analyzer units. The CBM database 152 includes specific data for each CBM-containing analyte (protein, allergen, . . . ) of interest. The specific data for each CBM-containing analyte (protein, allergen, . . . ) include data/information about the effect/change in a specific changeable parameter 116 of the sensing unit 110 due to the binding of the specific CBM-containing analyte (protein, allergen, . . . ) to the receptor (e.g. cellulose-based) 114. In other words, the CBM database 152 includes specific CBM-parameter-analyte- signatures for 1, . . . Q CBM-containing analytes (proteins, allergens, . . . ). The analyzer unit 140 is configured and operable to utilize the CBM database relating to specific changeable parameter, and process the output data 142 (typically one output data corresponding to one sensing data of the changeable parameter), to thereby find, according to the superposition principle, which specific CBM-containing analyte(s) (protein(s), allergen(s), . . . ), alone or combined, give(s) the output data obtained from the measurement unit 120.

The storage utility 150 can be any kind of storage memory known in the art. It can be a physical or virtual memory. In one particular example, the storage utility is a cloud storage configured to be accessed by the analyzer unit or the sensor device to exchange data therebetween.

The sensor device 100 is used to build the CBM database 152, by exposing one CBM-containing analyte of interest (protein, allergen, . . . ) to the sensor device each time and recording the corresponding sensing data/output data being indicative of a change in a parameter of the sensing unit due to the binding of the single CBM-containing analyte (protein, allergen, . . . ).

The feeding unit 130, which may be internal or external to the sensor device, can be configured for one or more different actions, including feeding the media under examination towards the sensing unit 110, removing of the media constituents that did not bind to the receptor 114 and preparing the sensing unit for another cycle of examination. In some embodiments, the media sample, e.g. a food sample, is firstly diluted in a suitable solvent (e.g. water, alcohol, etc.) to separate the different constituents and facilitate the chemical binding of the CBM-containing constituents to the sensing unit. Accordingly, the feeding unit 130 includes a feeding structure/utility 132 configured and operable for feeding the media towards the sensing unit in a predetermined and controlled rate, e.g. a feeding channel, tube or capillary. Further, the feeding unit 130 can include a washing structure/utility 134 configured and operable to wash the sensing surface with a suitable solvent (such as water, alcohol, etc.) and remove all of the unbound constituents before running the measurements by the measurement unit 120. Additionally, the feeding unit 130 can include a regeneration structure/utility 136 configured and operable to remove the bound constituents, i.e. the CBM-containing analyte(s) (protein(s), allergen(s), . . . ), e.g. by washing with a suitable fluid/solvent (such as water, alcohol, etc.), to thereby prepare the sensing unit for another examination cycle. Therefore, the sensor device 100 can be reusable.

Figure 1B:
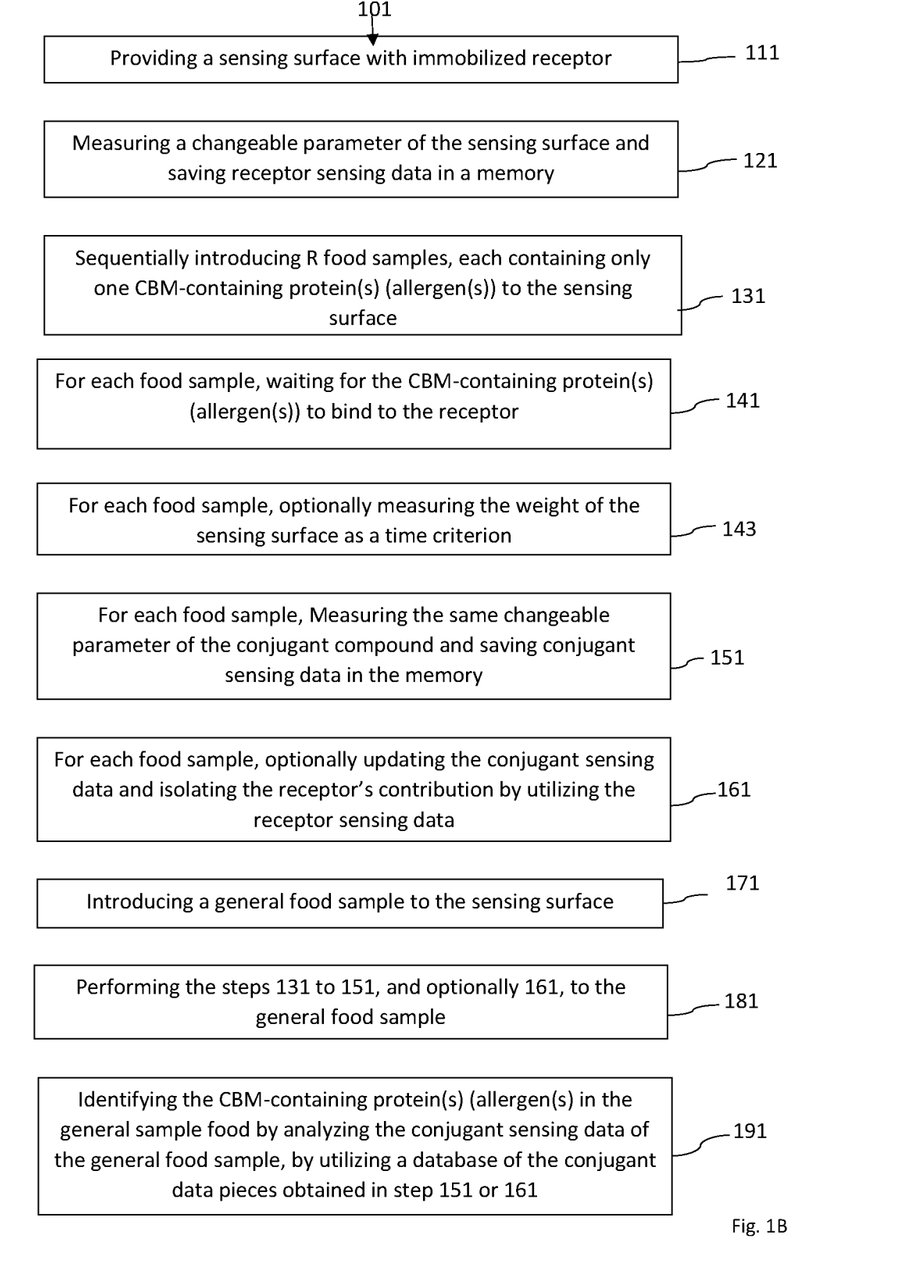
FIG. 1B illustrates a flow diagram of an example of a method of the invention for using sensing data for specific identification of one or more CBM-containing protein(s) in a media sample.

Reference is made to FIG. 1B illustrating a flow diagram 101 of an example of a method for specific identification of one or more CBM-containing protein(s) (allergen(s)) in a media sample, e.g. a food sample. At step 111, a sensing surface including an immobilized receptor that can specifically bind to a plurality of CBM-containing protein(s) (allergen(s)) 1, . . . R is provided. Non-limiting examples for such receptors include cellulose-containing carbohydrate compositions. At step 121, a changeable parameter of the sensing surface, including the receptor, is measured and the receptor sensing data is saved in a memory. For example, the permittivity/dielectric response of the sensing surface is measured and saved in a memory.

At step 131, R food samples, each including only one of the 1, . . . R CBM-containing protein(s) (allergen(s)) are sequentially introduced on the sensing surface to enable binding of the receptor to the specific CBM-containing protein(s) (allergen(s)). The food sample can be in gas, liquid or solid phase, though liquid phase is more suitable. It should be noted that, at this stage, each of the R food samples may be the pure CBM-containing protein(s) (allergen(s)) and does not need to contain any other food constituents. At step 141, for each food sample, waiting for enough time until a sufficient amount of the specific CBM-containing protein(s) (allergen(s)) binds to the receptor on the sensing surface. Optionally at step 143, the weight of the sensing surface is monitored in order to determine the time in which a sufficient amount of the specific CBM-containing protein(s) (allergen(s)) has bound to the receptor. At step 151, the same changeable parameter, as in step 121, is measured for the conjugant compound of both the receptor and the bound CBM-containing protein(s) (allergen(s)) and the conjugant's sensing data is saved in the memory. Steps 131 through 151 are repeated to cover each food sample, i.e. each one of the 1, . . . R CBM-containing protein(s) (allergen(s)), and corresponding conjugant sensing data pieces are saved in the memory.

At optional step 161, the 1, . . . R conjugant sensing data pieces are analyzed by comparing them to the receptor sensing data obtained in step 121. Updated conjugant sensing data pieces, in which the receptor sensing data is isolated are obtained and saved in the memory.

Steps 111 through 161 represent the building of a CBM database to be used for the specific identification of one or more CBM-containing analytes (protein(s) in a general food sample, allergen(s) in a general food sample, virus(es), etc.).

At step 171, a general food sample with unknown food constituents, is introduced to the sensing surface. At step 181, going through the same process as described in steps 131 to 151. If the optional step 161 was carried out, then it is also performed here with regards to general food sample.

At step 191, analytic algorithms including machine learning, superposition methods and possibly statistical methods, utilizing the CBM database, are applied to the conjugant sensing data obtained for the general food sample, in order to identify what specific one or more CBM-containing protein(s) (allergen(s)) exist in the general food sample and alert the user.

It is noted again that while the method described above concentrates on allergens in food samples, the same steps and principles, with the required adjustments, can be applied to identification of other CBM-containing analytes, such as specific kinds of viruses, in an examined media.

In the following figures, different exemplary embodiments of the sensor device and/or the sensor's units are described. It is noted that, units/utilities having the same general function as the units/utilities described in FIG. 1A are assigned similar reference numbers with additions of multiples of one hundred, e.g. 210 is a sensing unit having similar general functionality as the sensing unit 110, though some specific features may be added. A suffix letter can also be added to distinguish between different sub-figures, e.g. 210A and 210B are also assigned to sensing units having similar general functionality as the sensing unit 110.

Figure 2A:
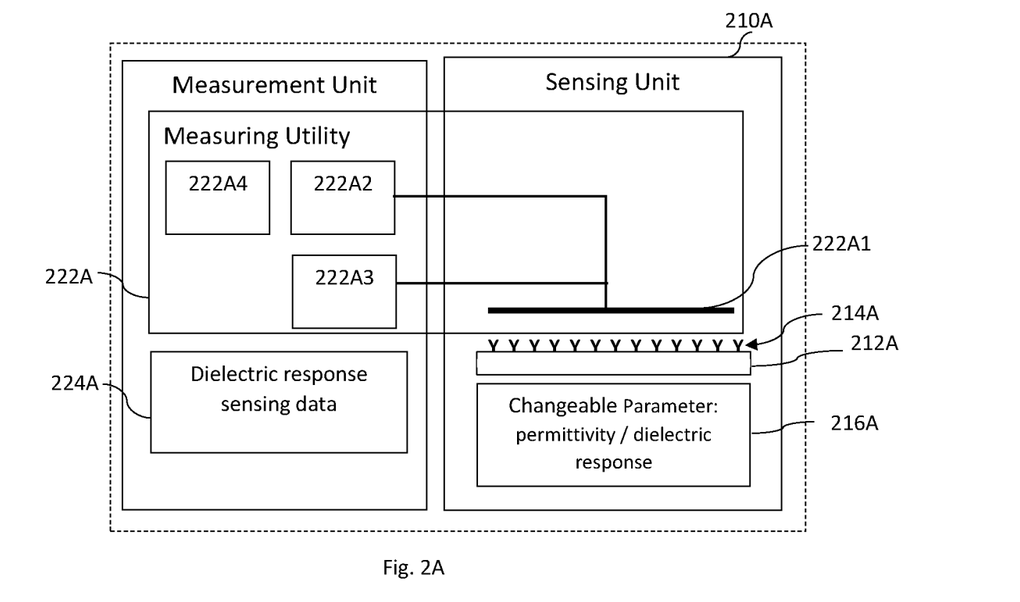
FIGS. 2A, 2B and 2D show three examples, respectively, of measuring utility of a measurement unit configured to monitor/measure three different changeable parameters of the sensing unit.

Reference is made to FIG. 2A illustrating a non-limiting example of a measuring utility of the measurement unit configured to monitor/measure a changeable parameter of the sensing unit, according to one non-limiting embodiment of the present invention. The changeable parameter 216A of the sensing unit 210A measured by the measuring utility 222A is the permittivity or the dielectric response of the sensing unit 210A. The measuring utility 222A includes an antenna structure 222A1, an electromagnetic wave generator/transmitter 222A2, and an electromagnetic wave receiver 222A3. Further, the measuring utility includes a controller 222A4 configured and operable to control the operation of the measuring utility 222A. The electromagnetic wave generator and receiver may be integrated in one device, and can be configured as a network analyzer as known in the art.

The antenna structure 222A1 is configured and operable to transmit predetermined electromagnetic wave(s), generated by the electromagnetic wave generator/transmitter 222A2, over a spectrum of frequencies, towards the sensing surface and to receive the reflected electromagnetic wave(s) and transmit it towards the electromagnetic wave receiver 222A3. Therefore, the antenna is located in the vicinity of the sensing surface 212A such that the sensing surface is exposed to the electromagnetic radiation transmitted by the antenna 222A1.

In some embodiments, as will be further described below, the antenna structure 222A1 also forms part of the sensing unit 210A, such that the antenna has at least a portion thereof pre-covered/pre-coated with the receptor 214A and as a result, any CBM-containing protein (allergen) in the media will also bind to the receptor 214A coated on the antenna 222A1, therefore enhancing the permittivity/dielectric response measurement results. The measuring utility 222A is configured and operable to activate the antenna 222A1 to produce electromagnetic radiation and receive the reflection thereof, before and after exposing the sensing unit to the media, via the electromagnetic wave generator 222A2 and receiver 222A3 respectively. The received electromagnetic signal is the permittivity/dielectric sensing data, indicative of the reflection coefficient S11, and may include changes in amplitude (real part) as well as phase (imaginary part) of the irradiated electromagnetic wave signal. The received electromagnetic signal is transmitted by the controller 222A4 to the analyzer unit (not shown) for analysis and processing. The electromagnetic wave generator 222A2 and receiver 222A3 are configured and operable with a predetermined frequency range, such that the dielectric response sensing data 224A transmitted to the analyzer unit is a spectrum of dielectric response of the receptor alone and of the conjugant receptor-CBM-containing analyte, when measured respectively before and after exposing the sensing unit 210A to the examined media. The dielectric response spectrum over a frequency range is characteristic to a specific material, in this case a CBM-containing analyte (protein, allergen, . . . ) and thus it can be used to specifically identify the involved CBM-containing analyte. By receiving both dielectric responses before and after the exposure to the media, it is possible to extract the dielectric response of the CBM-containing analyte(s) in the media. Through machine learning, by utilizing the superposition principle and the CBM database, the analyzer unit processes the dielectric response sensing data to generate output data indicative of the specific CBM-containing analyte(s) (protein(s), allergen(s), . . . ) included in the examined media.

Alternatively or additionally, though not specifically shown, the measuring utility 222A can include an electrode arrangement, instead of or in addition to the antenna. Such electrode arrangement may include a capacitor structure and the dielectric response of the sensing unit is measured/monitored by measuring/monitoring a change in the capacitance of the capacitor (capacitance value is defined by a given distance between two electrodes and their size, and dielectric property of media between them).

Considering the use of the capacitor structure instead of the antenna-based probe, for a given geometrical parameters of the capacitance structure, the change in the capacitance is associated with a change in the dielectric properties of the medium between electrodes.

It should be noted that the antenna-probe and capacitor structure may be used together. This may for example be used for providing two independent measurements for the verification purposes. It should also be noted that the sensing unit may include an electrodes' arrangement, configured such that one or more of the electrodes form part of a QCM resonator, while one or more other electrodes form part of the antenna structure.

Measurements of a dielectric response/properties of the media in the vicinity of an antenna are generally known, and by themselves do not form part of the present invention. For example, such measurements may utilize an open-ended coaxial probe method based on the use of a network analyzer, impedance analyzer, or transmission line techniques.

Figure 3A:
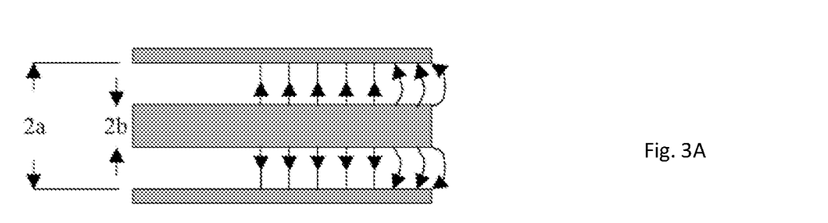
FIGS. 3A and 3B schematically illustrate the principles of configuration and operation of an open ended coaxial line probe for measuring dielectric properties of a medium.
Figure 3B:
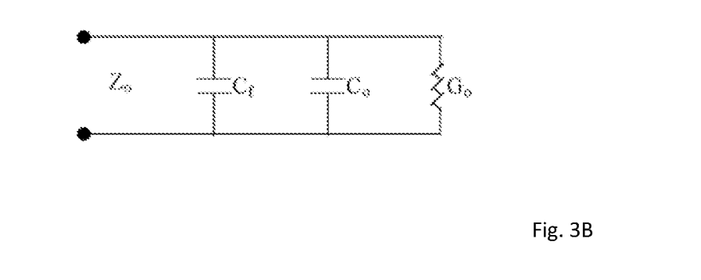

In such methods, the measurement circuit (probe) can be described by the equivalent circuit consisting of the fringing capacitance between the inner and outer conductor out of the coaxial structure and radiating conductance which represents propagation losses. This is schematically illustrated in FIGS. 3A and 3B showing open ended coaxial line probe and equivalent electrical circuit.

The capacitance and conductance are frequency and permittivity dependent and also dependent on the dimensions (inner and outer diameters) of the probe. The input admittance Y of the coaxial transmission line is related to the measured reflection coefficient $S_{11}$:

$$Y = Y_0 \frac{1 - S_{11}}{1 + S_{11}}$$

and related to the dielectric permittivity $\varepsilon_c$ of the media at angular frequency $\omega$:

$$Y/Y_0 j\omega C_f Z_o + j\omega \varepsilon C_o Z o + G_o Z o \varepsilon^{5/2}$$

wherein 2a and 2b are inner and outer diameters of the structure, $C_f$ and $C_o$ are internal and external fringing capacitors, $G_0$ is the radiation conductance, and $Z_o = 1/Y_0$ is the characteristic impedance of the coaxial line.

Hence, $$Y/Y_o = (1 - S_{11})/(1 + S_{11})$$

$$\varepsilon = (j\omega C_f Z_o)^{-1} \cdot (1 - S_{11})/(1 + S_{11}) \cdot (1 + C_f/C_o) - C_f/C_o$$

where $$C_t = C_f + C_{0,} \varepsilon = \varepsilon_o \varepsilon_r$$

and $$\varepsilon_r = \varepsilon'_r - j\varepsilon''_r$$

$\varepsilon'_r$ being the dielectric constant and $\varepsilon''_r$ being the loss factor.

Thus, the network analyzer or impedance analyzer is first calibrated, and then measures a complex reflection coefficient $S_{11}$. Then, the above equations are used to derive the dielectric property of the media.

Thus, any known suitable technique can be used, with the proper calibration, to detect and identify CBM-containing analyte(s) (protein(s), allergen(s), . . . ) included in a media, by measuring the dielectric response of the receptor-CBM-containing analyte(s) (protein(s), allergen(s), . . . ) conjugant.

Figure 2B:
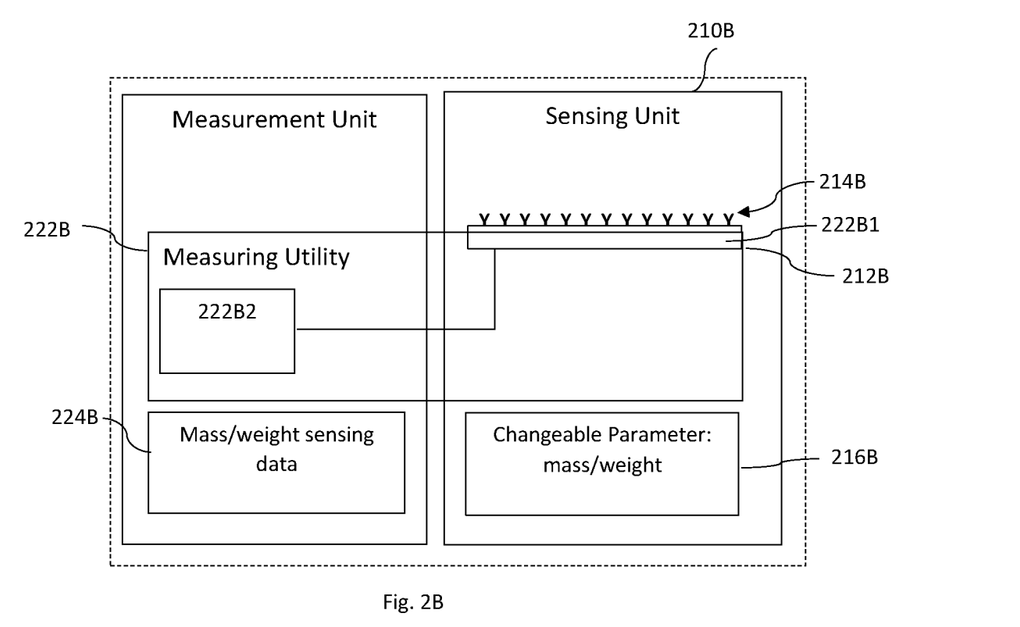

Reference is made to FIG. 2B illustrating another non-limiting example of a measuring utility of the measurement unit configured to monitor/measure another changeable parameter of the sensing unit, according to another non-limiting embodiment of the present invention. The changeable parameter 216B of the sensing unit 210B measured by the measuring utility 222B is the mass/weight of the sensing unit 210B. The mass/weight of the sensing unit 210B can be measured by different techniques known in the art. One specific technique presented in FIG. 2B is monitoring/measuring the mass/weight parameter indirectly by monitoring/measuring a frequency or resonance condition of the sensing unit 210B.

As shown, the measuring utility 222B includes a quartz crystal microbalance (QCM) resonator 222B1 and a controller 222B2. The QCM resonator 222B1 is placed in the vicinity of/attached to/embedded in the sensing surface 212B of the sensing unit 210B, such that binding of CBM-containing analyte(s) (protein(s), (allergen(s), . . . ) to the receptor 214B causes a change in the resonance frequency of the QCM resonator 222B1 that can be measured and quantified. The working principles of the QCM resonator and the way of extracting the mass/weight information is well known in the art and need not be described herein in detail. The use of a QCM resonator is beneficial due to its high sensitivity and resolution by being capable of measuring very small mass/weight densities down to a level of below 1 μg/cm². The resonance condition, indicative of the change in mass/weight, sensing data 224B, being output from the QCM resonator as an electrical signal, is transmitted by the controller 222B2 to the analyzer unit 240B for analysis and processing to thereby determine whether CBM-containing analyte(s) (protein(s), allergen(s), . . . ) has bound to the receptor 214B. It is noted that one advantage for measuring the mass/weight parameter of the sensing unit 210B is using this parameter as a timer. As described above, the media constituents are floating in a liquid solvent, consequently it will take time for the different constituents to sink towards the sensing surface 212B and to bind to the receptor 214B. Additionally, it is important to wait for enough amount of bound CBM-containing analyte(s) (protein(s), allergen(s), . . . ) before carrying out measurements, in order to acquire a reasonably good response/change in the monitored changeable parameter such as the dielectric property of the sensing unit. By monitoring the change in the mass/weight of the sensing unit, it is possible to define the time after which the dielectric measurements take place to obtain meaningful results.

Figure 2C:
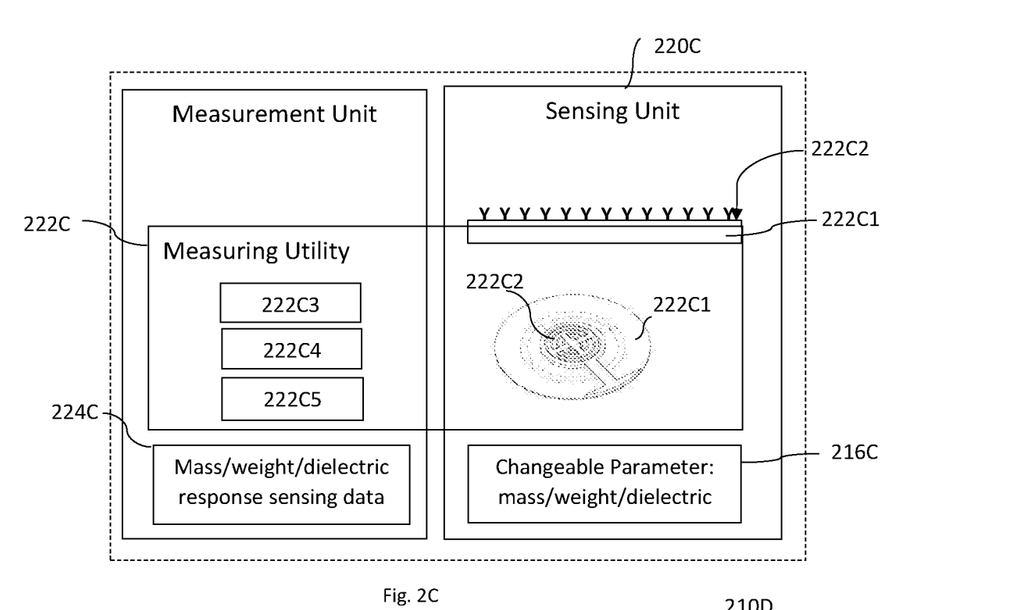
FIG. 2C illustrates yet another example of a measuring utility of the measurement unit configured to monitor/measure more than one changeable parameter of the sensing unit.

Reference is made to FIG. 2C illustrating yet another non-limiting example of a measuring utility of the measurement unit configured to monitor/measure more than one changeable parameter 216C of the sensing unit 220C and to generate corresponding pieces of sensing data 224C, according to a non-limiting embodiment of the present invention. As shown, the measuring utility 222C includes both a mass/weight measuring element, specifically a QCM resonator 222C1, and dielectric response measuring elements, by reflection, e.g. an antenna structure 222C2, an electromagnetic wave generator 222C3 and an electromagnetic wave receiver 222C4. The measuring utility also includes a controller 222C5 configured and operable to control the operation of the measuring utility 222C. While, it is possible to include, as described above, more than one independently working measuring utility in the measurement unit of the sensor device, the measuring utility 222C has advantageously an integrated measuring structure, in which the antenna 222C2 is printed on one of the QCM resonator's electrodes as in the illustrating figure showing an isometric upper view of the QCM resonator 222C1. This saves space, as well as improves signal-to-noise and spatial resolution of measurements. In this case, the controller 222C5 monitors the change in the mass/weight parameter, measured by the QCM resonator, and only after a predetermined threshold is reached, the controller 222C5 enables and activates the dielectric response measurements. Again, using one controller in the measuring utility can save space, time and power.

Figure 2D:
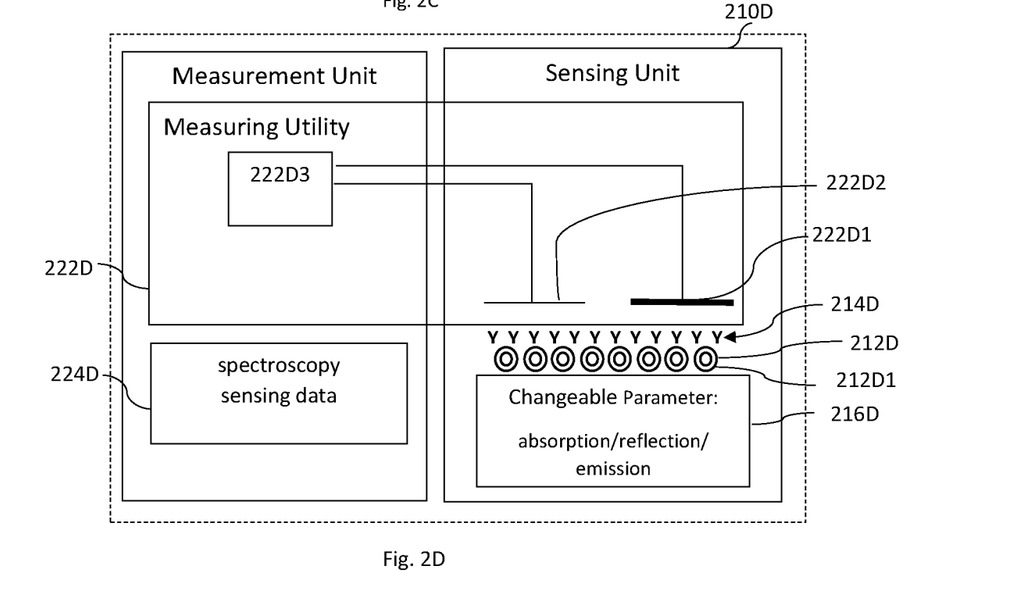

Reference is made to FIG. 2D illustrating another non-limiting example of a measuring utility of the measurement unit configured to monitor/measure a changeable parameter of the sensing unit, according to another non-limiting embodiment of the present invention. The changeable parameter 216D of the sensing unit 210D measured by the measuring utility 222D is the electromagnetic radiation absorbance/reflectance/emittance of the sensing unit 210D, in particular Infrared(IR)/ultraviolet(UV)/visible light(VL) (photo) absorption/reflection/emission. In other words, the measuring utility is configured to enable spectroscopy measurements. The measuring utility 222D includes a radiation source 222D1 configured and operable for irradiating the sensing surface 212D of the sensing unit by electromagnetic radiation of a predetermined frequency/wavelength range, specifically in one or more of the IR/UV/VL and a detector 222D2 configured for receiving radiation reflected/emitted from the sensing surface (together with the receptor and together with the receptor and the analyte). Therefore, the radiation source 222D1 and detector 222D2 are located in the vicinity of the sensing surface 212D to enable irradiating the sensing surface with the predetermined electromagnetic radiation and receiving the reflected/emitted radiation.

Further, the measuring utility includes a controller 222D3 configured and operable to control the operation of the measuring utility 222D. The controller 222D3 is also configured and operable to transmit the sensing data 224D received from the detector 222D2 to the analyzer unit (not shown) for carrying out spectroscopy analysis of the sensing data 224D. The controller 222D3 is configured and operable to activate the source 222D1 to produce radiation of the predetermined spectrum range towards the sensing surface 212D carrying the receptor 214D and the detector 222D2 to receive the radiation reflection/emission thereof, before and after exposing the sensing unit to the media. The source 222D1 and detector 222D2 are configured and operable with a predetermined frequency range(s), such that the sensing data 224D transmitted to the analyzer unit is a spectrum of absorption/reflection/emission of the sensing surface and/or the receptor 214D alone and of the conjugant receptor-CBM-containing analyte, when measured respectively before and after exposing the sensing unit 210D to the examined media. The absorption/reflection/emission spectrum over a frequency range is characteristic to a specific material, in this case a CBM-containing analyte (protein, allergen, . . . ) and thus it can be used (e.g. by building a database) to specifically identify the involved CBM-containing analyte. By receiving both reflections/emissions before and after the exposure to the media, it is possible to extract the effect of the CBM-containing analyte(s) in the media on the received spectrum. Through machine learning, by utilizing the superposition principle and the CBM database, the analyzer unit processes the sensing data to generate output data indicative of the specific CBM-containing analyte(s) (protein(s), allergen(s), . . . ) included in the examined media.

In some embodiments, the sensing data 224D includes photoluminescence (PL) (fluorescence, emission) of the sensing surface when being loaded/coated with the receptor and when the analyte(s) bind(s) to the receptor. In the specific non-limiting example shown in FIG. 2D, the sensing surface comprises carbon nanotubes 212D1, specifically single-wall carbon nanotubes (SWCN) arranged in the sensing surface and pre-coated/preloaded with the receptor 214D. SWCN are known for their IR and near-IR photoluminescence when being excited by an impinging radiation of a suitable spectrum range. It was shown that the SWCN exhibit a shift in the PL when other chemicals bind to it. It was also shown that the sensitivity of the SWCN's PL is very high down to the single molecule binding thereto. Utilizing the measuring utility 222D, the PL of the sensing surface comprising the SWCN is measured prior to exposure to the media containing the analyte(s) and after exposure. The shift in the frequency of the detected PL after the analyte(s) bind(s) to the receptor on the SWCN is indicative of the analyte(s). (see, for example: Daniel A. Heller, et al. (2011) Peptide secondary structure modulates single-walled carbon nanotube fluorescence as a chaperone sensor for nitroaromatics. 8544-8549 PNAS vol. 108 no. 21).

As mentioned above, the sensor device of the invention can be provided with more than one measuring utility some of which have been exemplified above. However, it should be understood that the invention is not limited to the above mentioned changeable parameters and any changeable parameter may be practiced with the invention.

Furthermore, in some embodiments of the invention, the changeable parameter can be, ultimately or additionally, labeling and/or staining with light the analyte, that is bound already to the receptor, by the use of antibodies specific to the analyte under question. This technique may potentially increase the sensitivity/specificity of the sensor device of the invention. The described technique can be as follows: after the media is exposed to the sensing surface of the sensing unit, and after the analyte binds to the receptor on the sensing surface, all the unbound media is washed out by the use of the washing utility. Then a media containing antibody(ies) specific to the analyte(s) under question is introduced such that the antibody(ies) bind exclusively to their matching analyte(s). The detection of the antibody(ies), and consequently the analyte(s) can be by any technique known in the art. For example, the antibody(ies) may have already been stained with a specific visible color, or may have been stained with fluorescent agents detectable in the UV spectrum. In any case, the changeable parameter, which is a change of the color of the analyte(s) due to the antibody(ies) binding to the analyte(s), is detectable as a sole or additional detection parameter.

Figure 4:
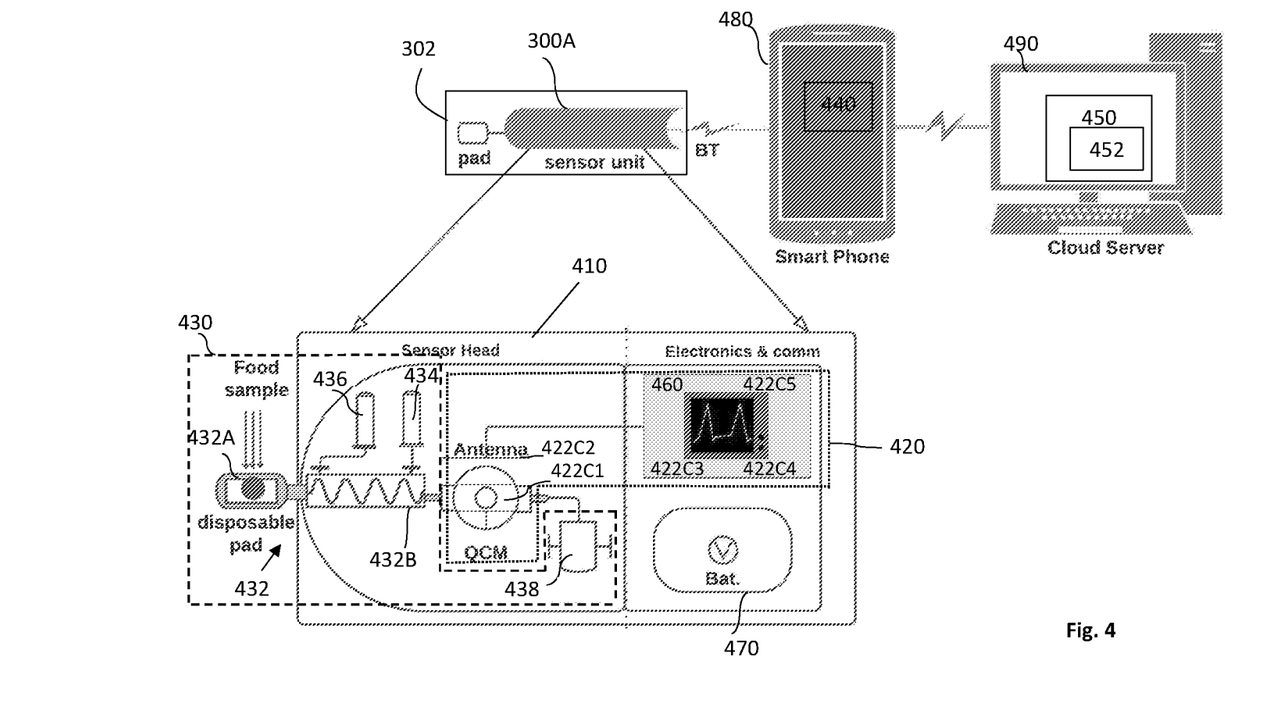
FIG. 4 illustrates a specific example of the configuration and operation of the sensing system of the invention implemented using cloud computing technique.

Reference is made to FIG. 4 showing schematically, by way of a block diagram, a non-limiting exemplary embodiment of the sensor device of the present invention. The sensor device 300A may be configured to be located inside a hand-held probe device 302 of any suitable configuration such that the user holds it in the hand to bring it in proximity to a food to be examined. As exemplified in the figure, the sensor device may be located inside (or (removably) mountable on) a user personal communication device, such as smartphone, which in turn is installed with an application program interface (API) preprogrammed for at least partially processing and analyzing the sensing data, and/or being in data communication, via computer network, with a cloud computer (server) for communicating the sensing data and/or the results of the data analysis. This will be described more specifically further below.

The sensor device 300A is configured, for example, for scanning the food from a predetermined distance (however without a need for physical contact with the food), to cause that the food constituents are ejected from the food sample towards the sensor device 300A. It is a known fact that when the food is warmed up to a certain temperature, the water in it starts to evaporate and together with the water some of the food constituents may potentially be ejected from the food. The invention may utilize this fact such that the sensor device 300A includes heating utilities to cause local and effective evaporation of the water and ejection of the food constituents towards the sensor device 300A to interact with the sensing media therein. Then, the sensing and measurement units of the device will be able to determine whether any CBM-containing protein(s) (allergen(s)) are present in the food. The ejection of the food constituents from the food sample can be performed by one or more of the following utilities that can be included in the hand-held probe 302: a heating utility configured and operable for direct heating of the food sample, an ultrasound utility configured and operable to irradiate the food with ultrasound waves which cause collisions between the food constituents and which will eventually heat the food, and/or a ventilation utility configured and operable to introduce air flow towards the food causing for small food pieces to fly towards the sensor device 300A.

The sensor device may be associated with (connectable to) external analyzer unit and external storage utility, as was described above with reference to FIG. 1A. Accordingly, the sensor device is called herein a sensor system, while it should be noted, that other implementations in which the sensor device includes all of the units/utilities in one enclosure and may then be referred to equally as a device or a system.

Thus, the sensor system includes a sensor device, e.g. device 300A exemplified in FIG. 4, an external analyzer unit (140 in FIG. 1A) and an external storage utility 152. The sensor device 300A includes a sensing unit (sensor head) 410 and a measurement unit 420 configured and operable as described above in FIG. 2C. The sensing unit has a sensing surface located on/formed by the upper side of a QCM resonator 422C1 that forms part of the measuring utility, on the sensing surface of the QCM resonator a thin film of a receptor (e.g. nano-cellulose) is coated. The measuring utility 422C also includes an antenna 422C2 coated with the receptor as well, and an electromagnetic wave generator 422C3, an electromagnetic wave receiver 422C4 and a controller 422C5 all three located in one enclosure.

A feeding unit 430 is also included (partially) in the sensor device 300A. The feeding unit 430 includes a feeding utility 432, a washing/rinsing utility 434 and a regeneration utility 436. The feeding utility 432 includes a feeding disposable pad 432A configured to receive a sample of food to be examined, loaded thereon, and to be dismissed off after operation, and a feeding channel/capillary 432B connecting between the disposable pad 432A and the sensing surface of the QCM resonator 422C1. The feeding unit 430 also includes in this example a waste container 438 which receives all the media after the washing/rinsing and regeneration operations.

The sensor device 300A is also configured with a battery 470, e.g. a replaceable or rechargeable battery, so it can be mobile and portable without the need for continuous connection to a power outlet.

In the described example, the analyzer unit 440 is a software application (API) that runs on a computing device 480 which is in this case a smartphone. The sensor device 300A includes a communication unit 460 that communicates with the analyzer unit 440 in the smartphone, via Bluetooth, for example, to send the sensing data thereto.

Also, the storage utility 450 that includes the database 452 may be located on a cloud server 490 and is accessed by the smartphone 480 via wireless connection, either via Wi-Fi or cellular signal. The analyzer unit 440, as a smartphone application, is configured to send and receive data from the database 452, so that it can download and upload CBM related data as explained above, to thereby enable identification of the specific CBM-containing analyte(s) (protein(s), allergen(s), . . . ) existing in the examined media and bound to the sensing surface of the sensing unit.

The invention claimed is:

1. A sensor device for use in detection of one or more proteins, the sensor device comprising:
 at least one sensing unit carrying one or more carbohydrate-based compositions immobilized thereon to be exposed to a media when the sensor device is in use, the one or more carbohydrate-based compositions include one or more of the following: oxidized cellulose, nano-cellulose, regenerated cellulose, or crystalline cellulose, the at least one sensing unit having one or more parameters thereof changeable in response to binding between the one or more carbohydrate-based compositions and one or more carbohydrate binding modules of (CBM)-containing proteins in the media based on the CBM domain; and a measurement unit configured and operable to monitor at least one changeable parameter of the at least one sensing unit, and upon detecting a change in the at least one changeable parameter generating sensing data indicative of the change, thereby enabling specific identification of the one or more CBM-containing proteins in the media.

2. The sensor device according to claim 1, wherein the at least one sensing unit has at least two of the parameters thereof changeable in response to the binding between the one or more carbohydrate-based compositions and the one or more CBM-containing proteins in the media, and wherein the measurement unit is configured and operable to monitor a first changeable parameter of the at least two changeable parameters, and upon detecting a first change in the first parameter generating a first sensing data indicative of the first change and enabling monitoring a second changeable parameter of the at least two parameters and generating a second sensing data indicative of the second change, the sensing data comprising the first and second sensing data.

3. The sensor device according to claim 1, wherein the at least one sensing unit includes an antenna structure, and wherein the one or more changeable parameters include permittivity reflection parameter of the antenna structure.

4. The sensor device according to claim 1, wherein the at least one sensing unit comprises a capacitor, and wherein the one or more changeable parameters include capacitance of the capacitor.

5. The sensor device according to claim 1, wherein the one or more changeable parameters of the at least one sensing unit includes weight of one or more parts of the at least one sensing unit.

6. The sensor device according to claim 1, wherein the at least one sensing unit includes a quartz crystal microbalance (QCM) resonator, and wherein the one or more changeable parameters include frequency and/or resonance condition of the quartz crystal microbalance (QCM) resonator.

7. The sensor device according to claim 6, wherein the at least one sensing unit includes an antenna structure integrated in the quartz crystal microbalance (QCM) resonator.

8. The sensor device according to claim 1, being configured and operable to communicate with an analyzer unit to convey the sensing data thereto, the analyzer unit being configured and operable to receive and analyze the sensing data, and generate output data indicative of the specific identification of the one or more CBM-containing proteins in the media, the analyzer unit having one of the following configurations: a) the analyzer unit is included in the at least sensor device, or b) the analyzer unit is external to the sensor device, the sensor device includes a communication unit configured and operable to communicate with the external analyzer unit to convey to the external analyzer unit the sensing data and identification data assigned to the sensor device.

9. The sensor device according to claim 1, wherein the analyzer unit is configured and operable to access database comprising data about a plurality of CBM-containing proteins, the data comprising, for each protein, an associated signature change of the one or more changeable parameters of the at least one sensing unit, to thereby determine whether the media contains specific one or more CBM-containing proteins.

10. The sensor device according to claim 1, configured and operable, when in use, to expose the at least one sensing unit to the media comprising one or more of the following foods: milk, eggs, soy, nuts, peanuts, sesame, wheat, celery, fish, or shellfish.

11. The sensor device according to claim 1, wherein the one or more CBM-containing proteins include one or more allergens.

12. The sensor device according to claim 1, further comprising a plurality of sensing units including sensing units carrying different kinds or amounts of carbohydrate-based compositions immobilized thereon to be exposed to same media, such that the one or more changeable parameters of the different sensing units change in a different way in response to the binding.

13. The sensor device according to claim 12, further comprising an analyzer unit configured and operable to receive the sensing data from each of the plurality of sensing units, and upon detecting a corresponding plurality of changes of the one or more changeable parameters of the at least one sensing unit, the analyzer unit generates a corresponding plurality of output data indicative of specific identification of the one or more CBM-containing proteins in the media.

14. The sensor device according to claim 1, wherein the at least one sensing unit is disposable.

15. The sensor device according to claim 1, further comprising one or more feeding mechanisms configured and operable for feeding a sample of the media towards the at least one sensing unit, feeding washing agent media that removes materials that did not bind to the immobilized carbohydrate-based composition, and/or feeding a regeneration agent that removes materials that have bound to the immobilized carbohydrate-based composition, to thereby prepare the at least one sensing unit for another detection cycle.

16. The sensor device according to claim 15, wherein the one or more feeding mechanisms include one or more of the following: a heating utility, an ultrasonic utility, or a ventilation utility.

17. The sensor device according to claim 1, wherein the at least one sensing unit is configured and operable to be exposed to the media being in gas or liquid phase.

18. A hand-held probe comprising the sensor device of claim 1, the hand-held probe being configured to be brought in proximity to the media when in use.

19. An allergen detection system being part of or connected to a communication network, the system comprising:
one or more sensor devices each of which is configured as the sensor device of claim 1;
an input utility configured and operable for independently receiving, via the network, one or more input data pieces including sensing data from the one or more sensor devices;
a processor utility configured and operable for analyzing the input data pieces, and determining for each of the input data pieces whether the respective sensing data is indicative of the sensing device interacting with a media containing allergen, the analyzing comprising: for the sensing data piece being indicative of a change in one or more of the changeable parameters of the at least onesensing unit in the sensor device, determining whether the change corresponds to a condition of the media classifying the media as allergen-containing media, the determining comprising accessing database comprising data about a plurality of allergens comprising, for each allergen, an associated signature change of the one or more parameters of the at least one sensing unit; and an output utility configured and operable for generating output data indicative of the allergen, to be transmitted via the network to a user of the respective sensor device.

20. A sensor device for use in detection of one or more proteins, the sensor device comprising:

at least one sensing unit carrying one or more carbohydrate-based compositions immobilized thereon to be exposed to a media when the sensor device is in use, the at least one sensing unit having one or more of parameters thereof changeable in response to binding between the one or more carbohydrate-based compositions and one or more carbohydrate binding modules of (CBM)-containing proteins in the media based on the CBM domain wherein the one or more carbohydrate-based compositions include one or more of the following: oxidized cellulose, nano-cellulose, regenerated cellulose, or crystalline cellulose; and a measurement unit configured and operable to monitor at least one changeable parameter of the at least one sensing unit, and upon detecting a change in the at least one changeable parameter generating sensing data indicative of the change, thereby enabling specific identification of the one or more CBM-containing proteins in the media;

wherein the one or more changeable parameters of the at least one sensing unit include a dielectric property of one or more parts of the at least one sensing unit; and wherein the measurement unit is configured and operable to monitor the dielectric property over a frequency spectrum and generate the sensing data comprising a frequency spectrum response indicative of the one or more CBM-containing proteins in the media.

* * * * *